US012678066B2

(12) United States Patent
Bogdanowicz et al.

(10) Patent No.: US 12,678,066 B2
(45) Date of Patent: Jul. 14, 2026

(54) IMPEDANCE-CALIBRATED DIAGNOSTIC MEDICAL DEVICES

(71) Applicant: NOVASCAN, INC., Milwaukee, WI (US)

(72) Inventors: Les Bogdanowicz, Park Ridge, IL (US); Alexander Grycuk, Mt. Prospect, IL (US); Paul Richard Voith, Cedarburg, WI (US); William David Gregory, Charleston, SC (US)

(73) Assignee: Novascan, Inc., Milwaukee, WI (US)

( * ) Notice: Subject to any disclaimer, the term of this patent is extended or adjusted under 35 U.S.C. 154(b) by 579 days.

(21) Appl. No.: 17/397,896

(22) Filed: Aug. 9, 2021

(65) Prior Publication Data

US 2022/0233230 A1     Jul. 28, 2022

Related U.S. Application Data

(60) Provisional application No. 63/142,260, filed on Jan. 27, 2021, provisional application No. 63/142,242, (Continued)

(51) Int. Cl.
*A61B 5/0538* (2021.01)
*A61B 5/00* (2006.01)
(Continued)

(52) U.S. Cl.
CPC ............ *A61B 5/0538* (2013.01); *A61B 5/053* (2013.01); *A61B 5/4836* (2013.01);
(Continued)

(58) Field of Classification Search
None
See application file for complete search history.

(56) References Cited

U.S. PATENT DOCUMENTS

| 3,608,543 A | 9/1971 | Longini et al. |
| 4,690,152 A | 9/1987 | Juncosa |
| | (Continued) | |

FOREIGN PATENT DOCUMENTS

| DE | 10 2004 031 181 A1 | 1/2006 |
| JP | 2008-500087 A | 1/2008 |
| | (Continued) | |

OTHER PUBLICATIONS

Partial Search Report for Application No. PCT/US2022/014159 dated Apr. 5, 2022.

(Continued)

*Primary Examiner* — Michael R Bloch
(74) *Attorney, Agent, or Firm* — McDonnell Boehnen Hulbert & Berghoff LLP

(57) ABSTRACT

Various embodiments set forth medical devices. In some embodiments, the medical device includes an impedance bridge, an instrument head that includes one or more electrode pairs and a calibration impedance, and one or more wire pairs that couple the impedance bridge to the one or more electrode pairs and the calibration impedance. The disclosed medical devices compensate for impedance caused by extraneous factors arising from manufacturing and materials variances while measuring the impedance of tissue.

13 Claims, 7 Drawing Sheets

Related U.S. Application Data filed on Jan. 27, 2021, provisional application No. 63/142,247, filed on Jan. 27, 2021, provisional application No. 63/142,254, filed on Jan. 27, 2021.

(51) Int. Cl.

| | |
|---|---|
| *A61B 5/053* | (2021.01) |
| *A61B 10/04* | (2006.01) |
| *A61B 18/14* | (2006.01) |
| *A61B 18/00* | (2006.01) |

(52) U.S. Cl.
CPC .......... *A61B 5/4839* (2013.01); *A61B 5/6859* (2013.01); *A61B 5/72* (2013.01); *A61B 5/74* (2013.01); *A61B 5/7405* (2013.01); *A61B 5/742* (2013.01); *A61B 10/04* (2013.01); *A61B 18/14* (2013.01); *A61B 2018/00154* (2013.01); *A61B 2018/00672* (2013.01); *A61B 2018/00755* (2013.01); *A61B 2018/00988* (2013.01); *A61B 2018/144* (2013.01); *A61B 2560/0223* (2013.01); *A61B 2560/0228* (2013.01); *A61B 2560/0238* (2013.01); *A61B 2562/0209* (2013.01)

(56) References Cited

U.S. PATENT DOCUMENTS

| | | | |
|---|---|---|---|
| 5,928,159 | A | 7/1999 | Eggers et al. |
| 6,770,070 | B1 | 8/2004 | Balbierz |
| 10,758,151 | B2 | 9/2020 | Gregory et al. |
| 2003/0088189 | A1 | 5/2003 | Tu et al. |
| 2003/0109871 | A1 | 6/2003 | Johnson et al. |
| 2004/0158167 | A1 | 8/2004 | Smith et al. |
| 2004/0181165 | A1 | 9/2004 | Hoey et al. |
| 2006/0004301 | A1 | 1/2006 | Kasevich |
| 2006/0135953 | A1 | 6/2006 | Kania et al. |
| 2006/0161151 | A1 | 7/2006 | Privitera et al. |
| 2007/0219551 | A1 | 9/2007 | Honour et al. |
| 2008/0004543 | A1 | 1/2008 | Davies |
| 2008/0125772 | A1 | 5/2008 | Stone et al. |
| 2008/0249467 | A1 | 10/2008 | Burnett et al. |
| 2009/0264792 | A1* | 10/2009 | Mazar .................. A61B 5/0809 600/547 |
| 2011/0190659 | A1 | 8/2011 | Long et al. |
| 2013/0211280 | A1 | 8/2013 | Gregory et al. |
| 2014/0081255 | A1 | 3/2014 | Johnson et al. |
| 2014/0276573 | A1 | 9/2014 | Miesel et al. |
| 2014/0324065 | A1 | 10/2014 | Bek et al. |
| 2015/0126990 | A1 | 5/2015 | Sharma et al. |
| 2015/0216442 | A1 | 8/2015 | Lavy et al. |
| 2015/0289929 | A1 | 10/2015 | Toth et al. |
| 2018/0161577 | A1 | 6/2018 | Goedeke et al. |
| 2018/0177549 | A1 | 6/2018 | Harrington et al. |
| 2018/0206755 | A1 | 7/2018 | Gregory et al. |
| 2019/0000501 | A1 | 1/2019 | Nowroozi et al. |
| 2019/0117113 | A1 | 4/2019 | Curran |
| 2019/0216358 | A1* | 7/2019 | Gregory ............... G01N 27/026 |
| 2020/0237435 | A1 | 7/2020 | Prakash et al. |
| 2020/0253504 | A1* | 8/2020 | Shen ........................ A61B 5/01 |
| 2020/0297419 | A1 | 9/2020 | Fang et al. |
| 2021/0153771 | A1 | 5/2021 | Ting et al. |
| 2022/0233089 | A1 | 7/2022 | Bogdanowicz et al. |
| 2022/0276290 | A1* | 9/2022 | Novet ............... G01R 27/2629 |

FOREIGN PATENT DOCUMENTS

| | | |
|---|---|---|
| JP | 2008-504344 A | 2/2008 |
| JP | 2008-536650 A | 9/2008 |
| WO | 2005/115235 A1 | 12/2005 |
| WO | 2006/116091 A2 | 11/2006 |
| WO | 2009/019707 A1 | 2/2009 |
| WO | 2018/227165 A1 | 12/2018 |
| WO | 2020/221485 A1 | 11/2020 |
| WO | 2020/247619 A1 | 12/2020 |

OTHER PUBLICATIONS

International Search Report for Application No. PCT/US2022/014157 dated May 3, 2022.

International Search Report for Application No. PCT/US2023/71871 dated Jan. 12, 2024.

International Search Report for Application No. PCT/PCT/US2023/71871 dated Jun. 17, 2024.

Partial Search Report for Application No. PCT/US2023/071871, dated Apr. 11, 2024.

International Search Report for application No. PCT/US2022/014159 dated Jul. 20, 2022.

Non Final Office Action received for U.S. Appl. No. 17/412,973 dated Jun. 21, 2024, 39 pages.

Schwan, H.P., "Electrode Polarization Impedance and Measurements in Biological Materials", The Moore School of Electrical Engineering, 19 pages.

Gregory et al., "The Cole relaxation frequency as a parameter to identify cancer in breast tissue", © 2012 American Association of Physicists in Medicine, http://dx.doi.org/10.1118/1.4725172, 8 pages.

International Search Report for Application No. PCT/US2023/064362 dated Sep. 19, 2023.

International Search Report for Application No. PCT/US2023/064363 dated Sep. 19, 2023.

Extended European Search Report for Application No. 22746631.5 dated Nov. 20, 2024.

Extended European Search Report for Application No. 22746632.3 dated Nov. 20, 2024.

Baek et al., "Quantitative Determination of Arterial Pulse Wave Velocity by Noninterfering Bioimpedance Sensing", 33rd Annual International Conference of the IEEE, Aug. 30-Sep. 3, 2011, pp. 6442-6445.

Overney et al., "Impedance Bridges: from Wheatstone to Josephson", DOI: 10.1088/1681-7575/ AACF6C, Jun. 19, 2018, 15 pages.

Liu et al., "An Improved Device for Bioimpedance Deviation Measurements Based On 4-Electrode Half Bridge", Review of Scientific Instruments, DOI: 10.1063/1 .4963658, vol. 87, No. 10, Oct. 5, 2016, 9 pages.

Non Final Office Action received for U.S. Appl. No. 17/412,973 dated Dec. 16, 2024, 25 pages.

Non Final Office Action received for U.S. Appl. No. 17/695,748 dated May 28, 2025, 73 pages.

Non Final Office Action received for U.S. Appl. No. 17/412,973 dated Jun. 9, 2025, 23 pages.

Final Office Action received for U.S. Appl. No. 17/695,745 dated Jul. 7, 2025, 29 pages.

Final Office Action received for U.S. Appl. No. 17/412,973 dated Mar. 26, 2025, 25 pages.

Non Final Office Action received for U.S. Appl. No. 17/695,745 dated Mar. 19, 2025, 76 pages.

Non Final Office Action received for U.S. Appl. No. 17/732,390 dated Apr. 8, 2025, 79 pages.

\* cited by examiner

700

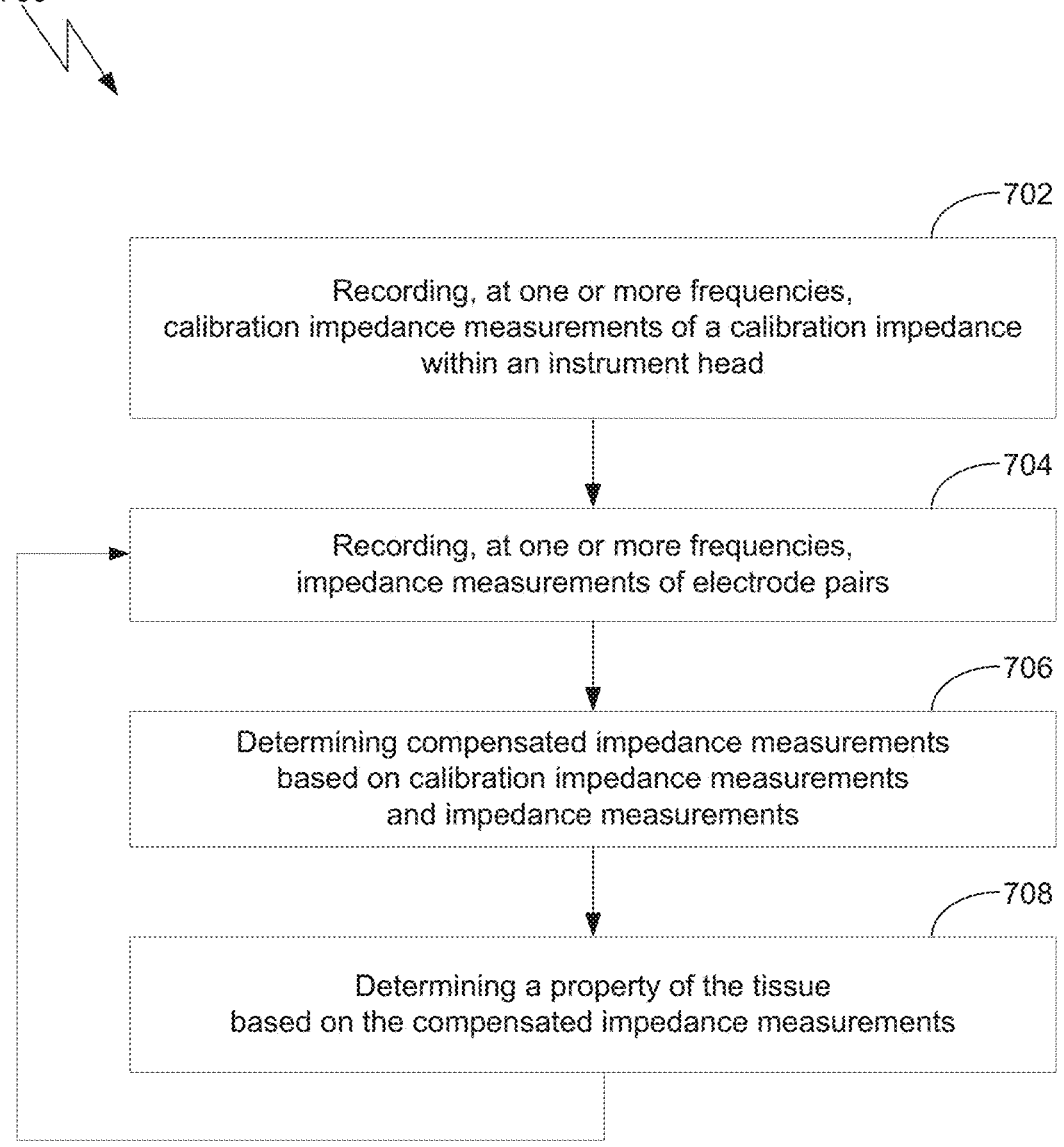

702

Recording, at one or more frequencies,
calibration impedance measurements of a calibration impedance
within an instrument head

704

Recording, at one or more frequencies,
impedance measurements of electrode pairs

706

Determining compensated impedance measurements
based on calibration impedance measurements
and impedance measurements

708

Determining a property of the tissue
based on the compensated impedance measurements

FIG. 7

IMPEDANCE-CALIBRATED DIAGNOSTIC MEDICAL DEVICES

CROSS-REFERENCES TO RELATED APPLICATIONS

The present application claims the benefit of U.S. Provisional Patent Application No. 63/142,242, filed Jan. 27, 2021; U.S. Provisional Patent Application No. 63/142,247, filed Jan. 27, 2021; U.S. Provisional Patent Application No. 63/142,254, filed Jan. 27, 2021; and U.S. Provisional Patent Application No. 63/142,260, filed Jan. 27, 2021. The subject matter of these related applications is hereby incorporated herein by reference.

BACKGROUND

Field of the Various Embodiments

Embodiments of the present disclosure relate generally to electronics and medical diagnostic technology and, more specifically, to impedance-calibrated diagnostic medical devices.

Description of the Related Art

In minimally invasive medical procedures, a healthcare provider inserts a medical instrument into the body of an individual and positions an instrument head of the medical instrument at a target location, such as a tumor. The instrument head includes, without limitation, a therapeutic drug delivery tool that delivers a therapeutic drug to the target location; an energy delivery tool that delivers energy (e.g., heat or electricity) to the target location; and/or a tissue sample extraction tool that extracts a tissue sample from the target location for further evaluation.

Delivering the therapeutic drug or energy to tissue other than the target location can result in failing to treat the target location or damaging healthy tissue. Therefore, some instrument heads include electrode pairs that measure an impedance of the tissue at the position of the instrument head. The medical device includes, without limitation, wires that couple the electrode pairs in the instrument head to external electrical components, including, without limitation, an impedance bridge. A processor measures the impedance of the tissue contacting the electrode pairs. A healthcare provider uses the measured impedance to determine a property of tissue contacting the electrode pairs.

One drawback of the medical devices described above is that various extraneous factors oftentimes alter the impedance measurements. The extraneous factors include, for example, variances in the materials and processes used to manufacture the medical device, such as the impedance bridge and the wires. The extraneous factors also can include the lengths and arrangements of the wires coupling the electrode pairs to the impedance bridge, electromagnetic interference near the wires, and mechanical factors, such as the length and bending of the wires. These types of extraneous factors can cause the electrical components of conventional medical devices to indicate an incorrect tissue type of the tissue at the position of the instrument head.

As the foregoing illustrates, what is needed in the art are more effective techniques for measuring tissue impedance.

SUMMARY

Embodiments are disclosed for impedance-calibrated diagnostic medical devices. In various embodiments, a medical device includes an impedance bridge, an instrument head that includes one or more electrode pairs and a calibration impedance, and one or more wire pairs that couple the impedance bridge to the one or more electrode pairs and the calibration impedance.

Embodiments are disclosed for determining a property of tissue. In various embodiments, a method includes recording, at one or more frequencies, one or more calibration impedance measurements associated with a calibration impedance that is included in an instrument head of a medical device; recording, at one or more frequencies, one or more impedance measurements associated with one or more electrode pairs that are included in the instrument head; determining one or more compensated impedance measurements based on the one or more calibration impedance measurements and the one or more impedance measurements; and determining the property of the tissue based on the one or more compensated impedance measurements.

Further embodiments provide, among other things, a system and a non-transitory computer-readable medium configured to implement the method set forth above.

At least one technical advantage of the disclosed medical device relative to the prior art is that the disclosed medical device compensates for the impedance caused by extraneous factors arising from manufacturing and materials variances while measuring the impedance of tissue. For example, the disclosed medical device is able to compensate for the lengths and bending of wires as well as related electromagnetic interference while measuring the impedance of tissue. Accordingly, the disclosed medical device measures tissue impedance more accurately than conventional medical devices, which typically do not implement similar impedance compensation techniques. Consequently, the disclosed medical device is able to determine properties of tissue, such as a Cole relaxation frequency, a tissue type, or an aggressiveness of a tumor tissue, more accurately than conventional medical devices. These technical advantages provide one or more technological advancements over prior art approaches.

BRIEF DESCRIPTION OF THE DRAWINGS

FIG. 7 is a flow diagram of method steps for determining a property of tissue, according to various embodiments.

DETAILED DESCRIPTION

In the following description, numerous specific details are set forth to provide a more thorough understanding of the various embodiments. However, in the range of embodiments of the concepts includes some embodiments omitting one or more of these specific details.

Figure 1:
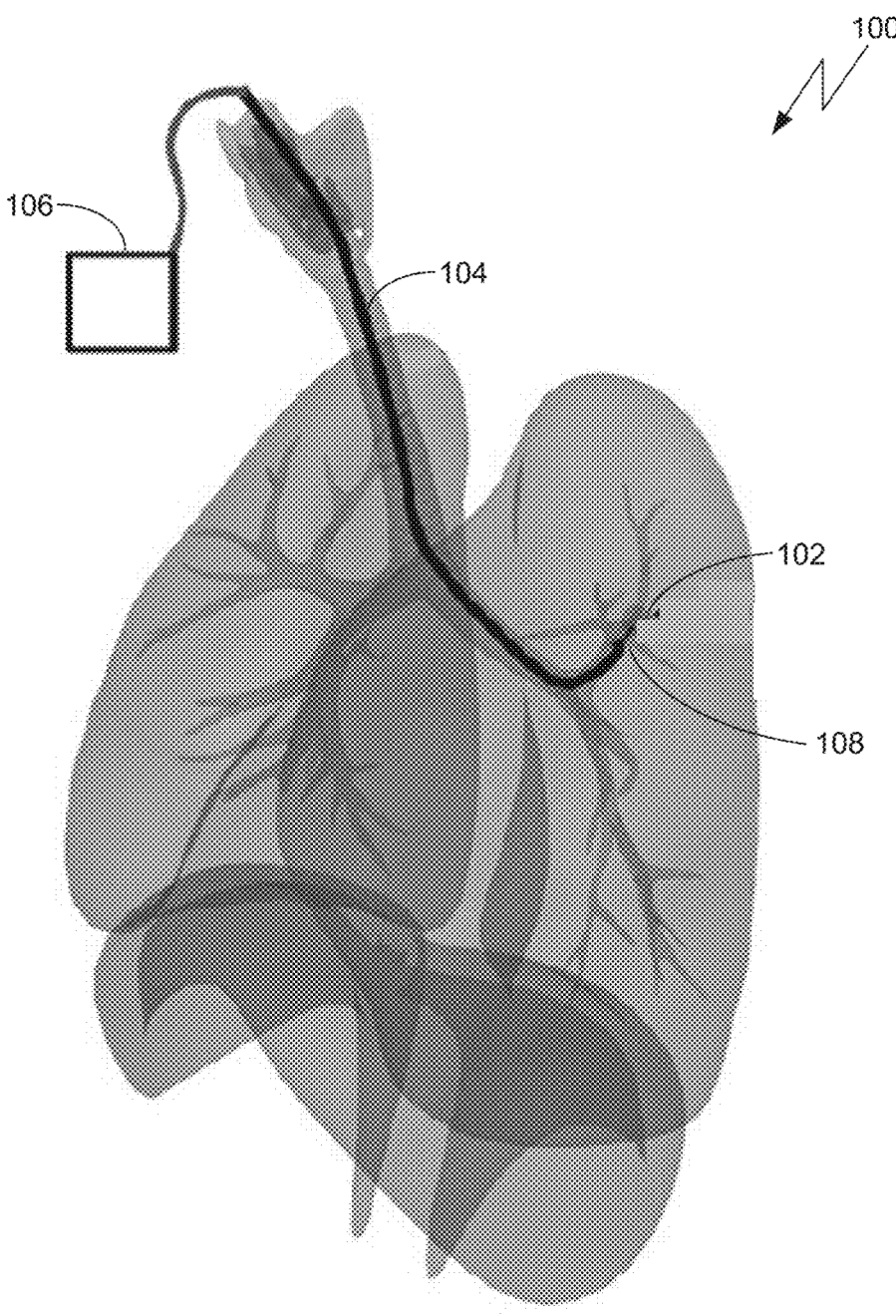
FIG. 1 illustrates a medical device 100, according to various embodiments.

FIG. 1 illustrates a medical device 100, according to various embodiments. As shown, the medical device 100 includes, without limitation, an instrument head 108, wires 104, and external electrical components 106. The instrument head 108 is positioned at a target location 102 (e.g., a location of a tumor). While not shown, the instrument head 108 includes, without limitation, an electrode pair and a tool that delivers a therapeutic drug or energy to the target location 102 and/or that extracts a tissue sample from the target location 102 for further evaluation. The external electrical components 106 generate current at various frequencies. The wires 104 conduct the current between the external electrical components 106 and the instrument head 108. The external electrical components 106 include a processor that measures the impedance of the electrode pair in the instrument head 108 and the tissue contacting the electrode pair. As described in greater detail below, the medical device 100 reports, to a healthcare provider during the minimally invasive medical procedure, a compensated impedance measurement and/or a property of the tissue contacting the electrode pair based on the compensated impedance measurement. The properties of the tissue can include, without limitation, a Cole relaxation frequency, which indicates a rate or frequency at which charges redistribute within a cell. The properties of the tissue can include, without limitation, a determination of a tissue type of the tissue contacting the electrode pair, such as a tumor or non-tumor determination, based on the Cole relaxation frequency. The properties of the tissue can include, without limitation, a determination of an aggressiveness of a tumor tissue of the tissue contacting the electrode pair, based on the Cole relaxation frequency.

Figure 2:
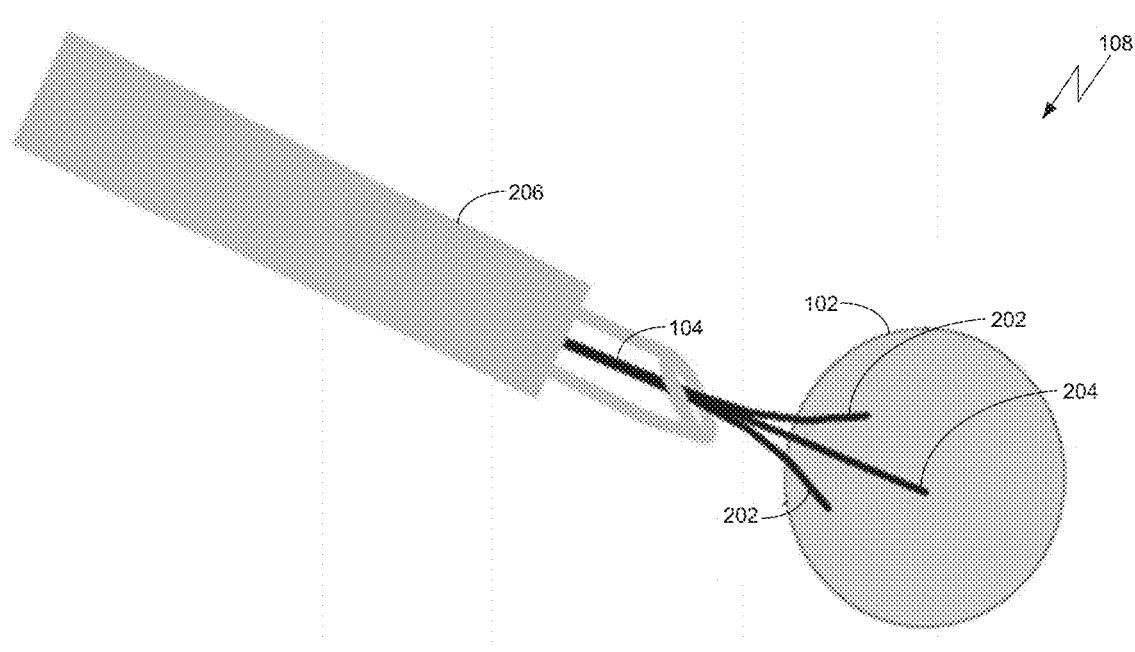
FIG. 2 is a more detailed illustration of the instrument head 108 of FIG. 1, according to various embodiments.

FIG. 2 is a more detailed illustration of the instrument head 108 of FIG. 1, according to various embodiments. As shown, the instrument head 108 includes, without limitation, an electrode pair 202, a tool 204, a catheter 206, and wires 104. The electrode pair 202 conducts current through tissue contacting the electrode pair 202 at various frequencies. The wires 104 conduct the current between the external electrical components 106 and the electrode pair 202 through the catheter 206. In various embodiments, the tool 204 delivers therapeutic drugs or energy (e.g., carried by a cannula or wires in the catheter 206) and/or extracts a tissue sample from the target location 102 for further evaluation. The elements of the instrument head 108 allow a healthcare provider to measure the impedance of the tissue contacting the electrode pair 202, in order to deliver the therapeutic drugs or energy to the target location 102 and/or to extract a tissue sample from the target location 102 for further evaluation.

Figure 3:
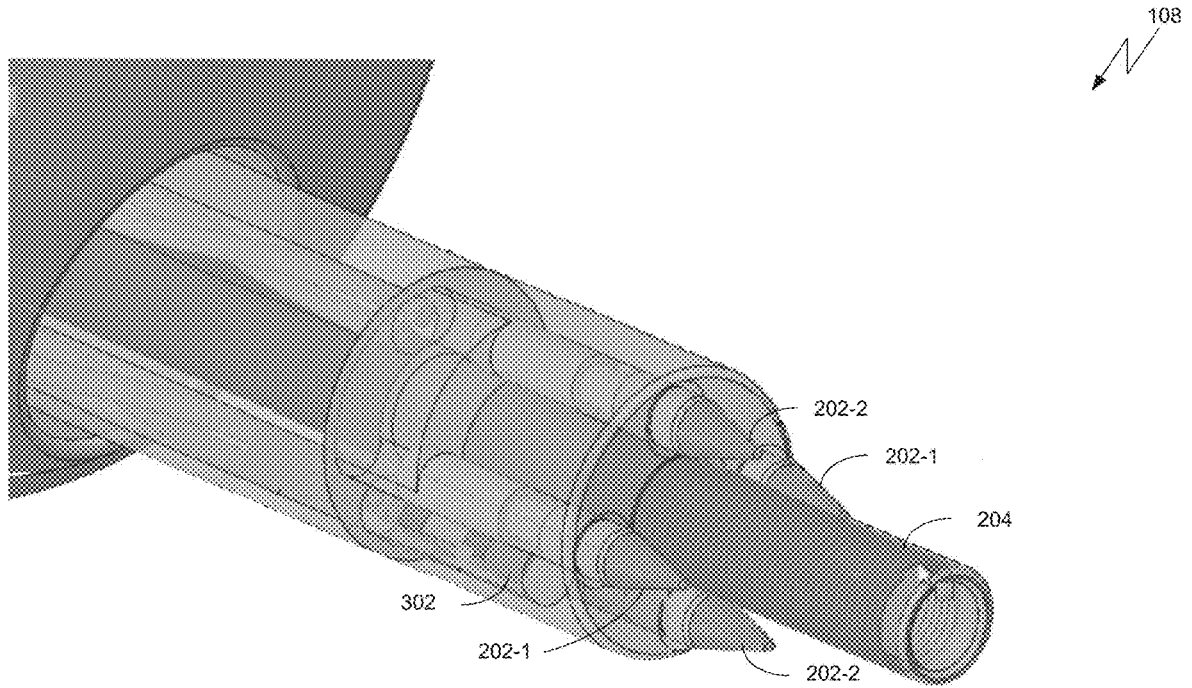
FIG. 3 is a more detailed illustration of the instrument head 108 of FIG. 2, including a calibration impedance 302, according to various embodiments.

FIG. 3 is a more detailed illustration of the instrument head 108 of FIG. 2, including a calibration impedance 302, according to various embodiments. As shown, the instrument head 108 includes, without limitation, a first electrode pair 202-1, a second electrode pair 202-2, a tool 204, and a calibration impedance 302. As shown, the instrument head 108 includes two electrode pairs 202-1, 202-2; however the term "electrode pair 202," as used herein, is to be understood to include various embodiments with any number of electrode pairs 202, including, without limitation, one electrode pair 202 or three or more electrode pairs 202. In various embodiments, the tool 204 includes, without limitation, a tool 204 that delivers a therapeutic drug or energy (e.g., heat or electricity) to the target location 102 and/or a tool 204 that extracts a tissue sample from the target location 102 for further evaluation.

In various embodiments, the calibration impedance 302 is an impedance load of a fixed and/or known impedance (i.e., a resistance and/or a reactance) that is included in the instrument head 108 during manufacturing. In various embodiments, the calibration impedance 302 includes, without limitation, two or more calibration impedance loads. For example, the calibration impedance loads can include, without limitation, a phase offset calibration impedance load (e.g., a 100-ohm resistor) to determine a phase offset of the calibration impedance 302); a coarse gain calibration impedance load (e.g., a 510-ohm resistor) to determine a coarse gain of the calibration impedance 302; a fine gain calibration impedance load (e.g., a 300-ohm resistor) to determine a fine gain of the calibration impedance 302; and/or a phase calibration impedance load (e.g., a 0-ohm resistor) to determine a phase of the calibration impedance 302.

Figure 4:
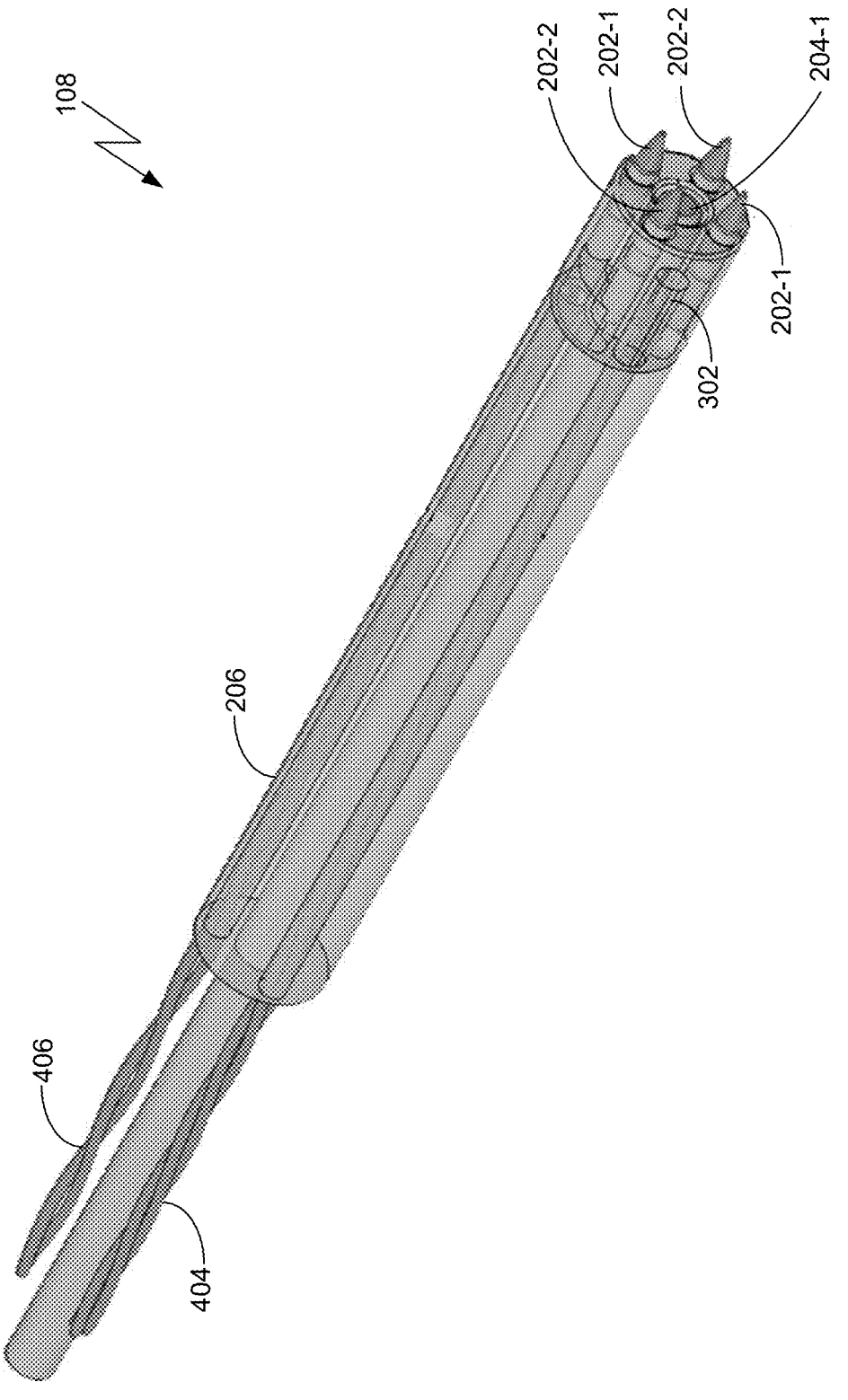
FIG. 4 is a more detailed illustration of the instrument head 108 of FIG. 2, including twisted wire pairs 404, 406, according to various embodiments.

FIG. 4 is a more detailed illustration of the instrument head 108 of FIG. 2, including twisted wire pairs 404, 406, according to various embodiments. As shown, the instrument head 108 includes, without limitation, a first electrode pair 202-1, a second electrode pair 202-2, a tool 204, a catheter 206, a calibration impedance 302, a calibration impedance twisted wire pair 404, and an electrode twisted wire pair 406. The calibration impedance twisted wire pair 404 conducts current between the calibration impedance 302 and the external electrical components 106. The calibration impedance twisted wire pair 404 includes, without limitation, a supply wire and a ground wire. The twisting of the calibration impedance twisted wire pair 404 reduces impedance due to electromagnetic interference along the length of the calibration impedance twisted wire pair 404. The electrode twisted wire pair 406 conducts current between the electrode pairs 202-1, 202-2 and the external electrical components 106. The electrode twisted wire pair 406 includes, without limitation, a supply wire and a ground wire. The twisting of the electrode twisted wire pair 406 reduces impedance due to electromagnetic interference along the length of the electrode twisted wire pair 406. In various embodiments, two or more of the electrode pairs 202-1, 202-2 share a supply wire and/or a ground wire of the electrode twisted wire pair 406. In some other embodiments, each of two or more the electrode pairs 202-1, 202-2 respectively has a supply wire and/or a ground wire in the electrode twisted wire pair 406. For example and without limitation, the instrument head 108 can include two electrode pairs 202, where each electrode pair 202 includes an electrode twisted wire pair 406 that couples the electrode pair to the external electrical components 106. Thus, each electrode pair 202 of the two electrode pairs 202 can be driven by a separate current source and referenced to a separate return lead, and the external electrical components 106 can record a four-lead impedance measurement.

While not shown, in various embodiments, the instrument head 108 includes, without limitation, a buffer circuit that is positioned close to the electrode pairs 202. The buffer circuit isolates an output of the electrode pairs 202 from parasitic capacitance due to the external electrical components 106 coupled to the output of the electrode pairs 202 by the electrode twisted wire pair 406. Alternately, in some embodiments, an output of the buffer circuit and an input of the impedance bridge 504 are coupled by analog-to-digital converter (ADC) circuitry that converts an analog output of the buffer circuit to a digital signal. The digital signal can be transmitted to the external electrical components 106 by media such as, without limitation, a cable or wire (e.g., fiber-optic cable) and/or wireless electromagnetic signals (e.g., Bluetooth). Converting the signal to a digital output further reduces extraneous effects, such as parasitic capacitance or ambient electromagnetic interference, on the quality of the signal.

Figure 5:
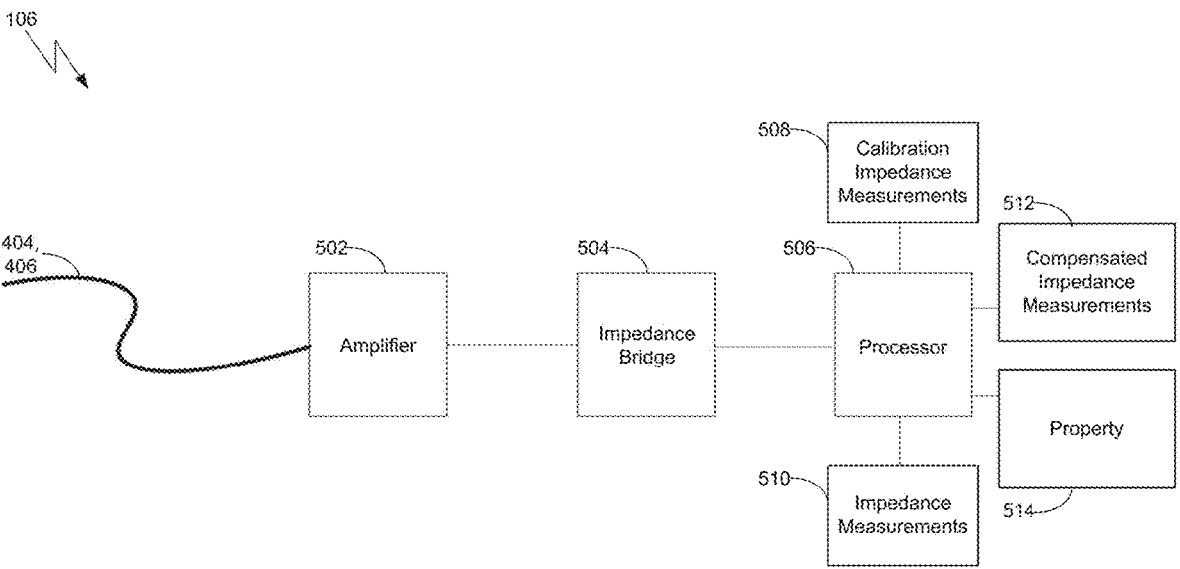
FIG. 5 is a more detailed illustration of the external electrical components 106 coupled to the instrument head 108 of FIG. 2, according to various embodiments.

FIG. 5 is a more detailed illustration of the external electrical components 106 coupled to the instrument head 108 of FIG. 2, according to various embodiments. As shown, the external electrical components 106 include a calibration impedance twisted wire pair 404, an electrode twisted wire pair 406, an amplifier 502, an impedance bridge 504, and a processor 506. The calibration impedance twisted wire pair 404 conducts current at various frequencies between the calibration impedance 302 and the external electrical components 106. The electrode twisted wire pair 406 conducts current at various frequencies between the electrode pair and the external electrical components 106. In various embodiments, the amplifier 502 is an analog interface amplifier that amplifies a supplied voltage and/or a return voltage while the calibration impedance twisted wire pair 404 conducts current at various frequencies between the impedance bridge 504 and the calibration impedance 302 and/or the electrode twisted wire pair 406 conducts current at various frequencies between the impedance bridge 504 and the electrode pair 202. In various embodiments, the impedance bridge 504 is an impedance load that the processor 506 measures to determine an impedance of a circuit including the impedance bridge 504, the amplifier 502, the calibration impedance twisted wire pair 404, and the instrument head 108 (e.g., the electrode pair 202 and/or the calibration impedance 302).

In various embodiments, the processor 506 measures an impedance of the impedance bridge 504 to determine an impedance of a circuit including the impedance bridge 504, the amplifier 502, the calibration impedance twisted wire pair 404, and the instrument head 108. The processor 506 generates frequencies for a current that the calibration impedance twisted wire pair 404 conducts between the impedance bridge 504 and the calibration impedance 302, and measures an impedance of the impedance bridge 504. While the calibration impedance twisted wire pair 404 conducts this current at various frequencies, the processor 506 records one or more calibration impedance measurements 508 of the circuit including the calibration impedance 302. In various embodiments, the calibration impedance measurements for each frequency include, without limitation, a phase offset measurement, a coarse gain measurement, a fine gain measurement, and/or a phase measurement. In various embodiments, the processor 506 records each measurement of the calibration impedance measurements 508 while the circuit includes one or more calibration impedance loads of the calibration impedance 302. In various embodiments, the calibration impedance loads include, without limitation, a phase calibration impedance load; a coarse gain calibration impedance load; a fine gain calibration impedance load; and/or a phase calibration impedance load. In various embodiments, the processor 506 measures and records one or more of the calibration impedance measurements 508 (e.g., the phase offset measurement, the coarse gain, and the phase) during a factory calibration process. In various embodiments, the processor 506 measures and records one or more of the calibration impedance measurements 508 (e.g., the fine gain) during a surgical calibration process.

The processor 506 generates frequencies for a current that the electrode twisted wire pair 406 conducts between the impedance bridge 504 and the electrode pair 202 and measures an impedance of the impedance bridge 504. While the electrode impedance twisted wire pair 406 conducts this current at various frequencies, the processor 506 records one or more impedance measurements 510 of the circuit including the electrode pair 202. In various embodiments, the frequencies of the current for the calibration impedance measurements 508 are the same as, similar to, or different than the frequencies for measuring the impedance measurements 510. For example, the processor 506 can measure the calibration impedance measurements 508 at each frequency of a first set of frequencies, and can measure the impedance measurements 510 at each frequency of a second set of frequencies that is different than the first set of frequencies.

In various embodiments, the processor 506 determines one or more compensated impedance measurements 512 based on the calibration impedance measurements 508 and the impedance measurements 510. For example, the processor 506 subtracts or divides the calibration impedance measurements 508 from the impedance measurements 510. The compensated impedance measurements 512 indicate the impedance of the tissue contacting the electrode pair 202

In various embodiments, the processor 506 determines a property 514 of tissue contacting the electrode pair 202 based on the compensated impedance measurements 512. In various embodiments, the property 514 includes, without limitation, a Cole relaxation frequency of the tissue; a tissue type of the tissue (e.g., a determination of the tissue as tumor or non-tumor); and/or an aggressiveness of a tumor tissue. For example, the Cole relaxation frequency is a frequency of a maximum normalized impedance measurement of tissue contacting the electrode pair 202. A determination of a Cole relaxation frequency below a threshold frequency (e.g., $10^5$ Hz) indicates an increased probability that the tissue contacting the electrode pair 202 is normal tissue. A determination of a Cole relaxation frequency above the threshold frequency indicates an increased probability that the tissue contacting the electrode pair 202 is a tumor. By determining the compensated impedance measurements 512, the processor 506 determines the property 514 based on the impedance of the tissue without the impedance due to the extraneous factors. In various embodiments, the processor 506 reports the property 514 to a user of the medical device 100. In various embodiments, the processor 506 controls a tool 204 of the instrument head 108 based on the property 514. For example, the processor 506 causes the tool 204 to deliver a therapeutic drug or energy to the target location 102 based on the compensated impedance measurements 512 indicating that the tissue contacting the electrode pair 202 is a tumor.

Figure 6:
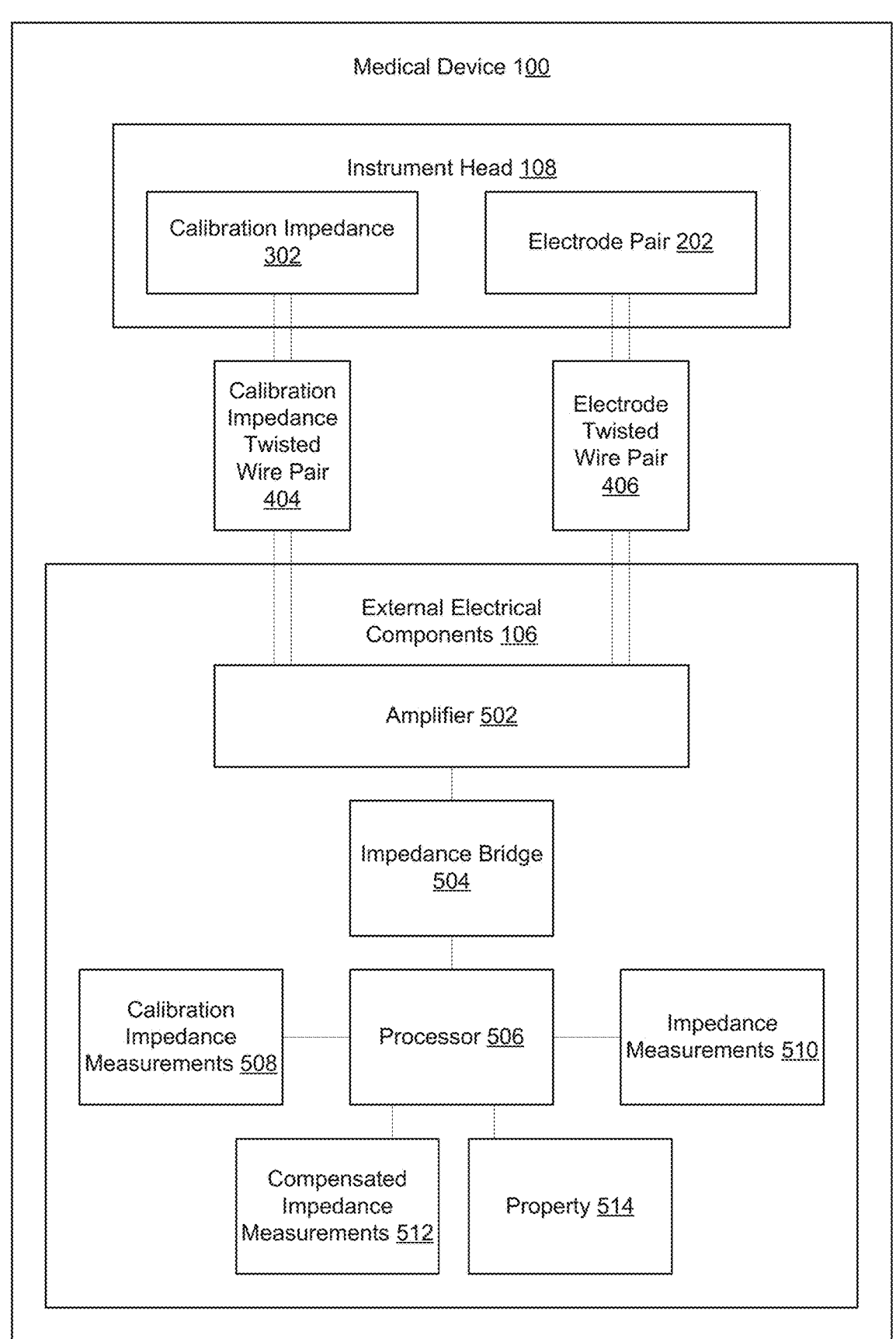
FIG. 6 is a more detailed illustration of the medical device 100 of FIG. 1, according to various embodiments.

FIG. 6 is a more detailed illustration of the medical device 100 of FIG. 1, according to various embodiments. As shown, the medical device 100 includes an instrument head 108 and external electrical components 106 coupled by a calibration impedance twisted wire pair 404 and an electrode twisted wire pair 406. As shown, the instrument head 108 includes a calibration impedance 302 and an electrode pair 202. The calibration impedance 302 includes, without limitation, one or more impedance loads of known and/or fixed impedance (e.g., resistance and/or reactance). In various embodiments, the instrument head 108 includes, without limitation, two or more electrode pairs 202 that share an electrode twisted wire pair 406, and/or two or more electrode pairs 202 respective coupled with an electrode twisted wire pair 406. While not shown, in various embodiments, the instrument head 108 includes, without limitation, a tool 204 that delivers a therapeutic drug or energy (e.g., heat or electricity) to the target location 102.

As shown, the external electrical components 106 include an amplifier 502, an impedance bridge 504, and a processor 506. The amplifier 502 amplifies a supplied voltage and/or a return voltage while the calibration impedance twisted wire pair 404 and/or the electrode twisted wire pair 406 conducts current at various frequencies between the impedance bridge 504 and the instrument head 108. The impedance bridge 504 is an impedance load that the processor 506 measures to determine an impedance of a circuit including the impedance bridge 504, the amplifier 502, the calibration impedance twisted wire pair 404 or the electrode twisted wire pair 406, and one or more components of the instrument head 108. The processor 506 records, at various frequencies, one or more calibration impedance measurements 508. The processor 506 records, at various frequencies, one or more impedance measurements 510. The processor 506 determines one or more compensated impedance measurements 512 based on the calibration impedance measurements 508 and the impedance measurements 510. Based on the compensated impedance measurements 512, the processor 506 determines a property 514 of tissue contacting the electrode pair 202. In various embodiments, the property 514 includes, without limitation, a Cole relaxation frequency of the tissue; a tissue type of the tissue (e.g., a determination of the tissue as tumor or non-tumor); and/or an aggressiveness of a tumor tissue. By determining the compensated impedance measurements 512, the medical device 100 determines the property 514 based on the impedance of the tissue without the impedance due to the extraneous factors. In various embodiments, based on the property 514, the medical device 100 reports the property 514 to a user of the medical device 100 and/or controls the tool 204 (e.g., to deliver a therapeutic drug or energy to the target location and/or to extract a tissue sample from the target location for further evaluation). For example, the medical device 100 displays an indicator of the property using a visual output (e.g., a liquid crystal display (LCD), a light-emitting diode (LED) display or indicator, or the like) and/or presents an audio indicator of the property using an audio output (e.g., using a speaker, buzzer, or the like to present an audio cue of the property of the device, such as a spoken description, sound effect, or the like).

FIG. 7 is a flow diagram of method steps for determining a property 514 of tissue, according to various embodiments. Although the method steps are described in conjunction with the systems of FIGS. 1-6, persons skilled in the art will understand that any system configured to perform the method steps, in any order, falls within the scope of the present invention.

As shown, a method 700 begins at step 702, where a processor 506 of a medical device 100 records, at one or more frequencies, one or more calibration impedance measurements 508 of a calibration impedance 302 within an instrument head 108 of the medical device 100. In various embodiments, the processor 506 can record the calibration impedance measurements 508 in a memory of the medical device 100, or in a memory of another device, such as a server. For example, the processor 506 can record the calibration impedance measurements 508 as part of a manufacturing process (e.g., by a vendor) and/or as part of a medical procedure. The calibration impedance measurements 508 indicate the impedance due to extraneous factors, including (without limitation) variance in the materials, electromagnetic interference, or the lengths or bending of the wires 104.

At step 704, the processor 506 records, at one or more frequencies, one or more impedance measurements 510 of one or more electrode pairs 202 within the instrument head 108. In various embodiments, the processor 506 record the impedance measurements 510 at the same or similar frequencies as the frequencies of the calibration impedance measurements 508, or at different frequencies (e.g., a more limited set of frequencies). The impedance measurements 510 indicate an impedance of tissue contacting the one or more electrode pairs 202 and impedance due to extraneous factors, as previously discussed.

At step 706, the processor 506 determines one or more compensated impedance measurements 512 based on the calibration impedance measurements 508 and the impedance measurements 510. In various embodiments, the processor 506 determines the compensated impedance measurements 512 by subtracting the calibration impedance measurements 508 from the impedance measurements 510, and/or by dividing the impedance measurements 510 by the calibration impedance measurements 508. The compensated impedance measurements 512 indicate an impedance of tissue contacting the one or more electrode pairs 202 without the impedance due to the extraneous factors.

At step 708, the processor 506 determines the property 514 of the tissue based on the one or more compensated impedance measurements 512. In various embodiments, the property 514 includes, without limitation, a Cole relaxation frequency of the tissue; a tissue type of the tissue (e.g., a determination of the tissue as tumor or non-tumor); and/or an aggressiveness of a tumor tissue. Performing the determining based on the compensated impedance measurements 512 enables the medical device 100 to determine the property 514 based on the impedance of the tissue without the impedance due to the extraneous factors. In various embodiments, the medical device 100 can use the determined property, for example, without limitation, by reporting the property 514 to a user of the medical device 100 and/or controlling the tool 204 based on the property 514. After step 708, the processor 506 returns to step 704 to record additional impedance measurements 510.

In sum, the disclosed medical device measures a calibration impedance in the instrument head to determine the impedance caused by extraneous factors. When the medical device subsequently measures the impedance of tissue contacting the electrode pair, the medical device compensates the tissue impedance measurements based on the calibration impedance measurements. This compensation technique advantageously reduces the impedance-altering effects of the extraneous factors on the impedance measurements of the tissue.

At least one technical advantage of the disclosed medical device relative to the prior art is that the disclosed medical device compensates for the impedance caused by extraneous factors arising from manufacturing and materials variances while measuring the impedance of tissue. For example, the disclosed medical device is able to compensate for the lengths and bending of wires as well as related electromagnetic interference while measuring the impedance of tissue. Accordingly, the disclosed medical device measures tissue impedance more accurately than conventional medical devices, which typically do not implement similar impedance compensation techniques. Consequently, the disclosed medical device is able to determine properties of tissue, such as a Cole relaxation frequency, a tissue type, or an aggressiveness of a tumor tissue, more accurately than conventional medical devices. These technical advantages provide one or more technological advancements over prior art approaches.

1. In some embodiments, a medical device comprises an impedance bridge, an instrument head that includes one or more electrode pairs and a calibration impedance, and one or more wire pairs that couple the impedance bridge to the one or more electrode pairs and the calibration impedance.

2. The medical device of clause 1, wherein the one or more wire pairs comprises at least one of a calibration impedance twisted wire pair that couples the calibration impedance with the impedance bridge or an electrode impedance twisted wire pair that couples the one or more electrode pairs with the impedance bridge.

3. The medical device of clauses 1 or 2, wherein the one or more electrode pairs includes two electrode pairs, the one or more wire pairs include two wire pairs, and each wire pair couples the impedance bridge to a different one of the two electrode pairs.

4. The medical device of any of clauses 1-3, wherein the instrument head further includes at least one of a therapeutic drug delivery tool, an energy delivery tool, or a tissue sample extraction tool.

5. The medical device of any of clauses 1-4, wherein the calibration impedance includes at least one of a phase offset calibration impedance load, a coarse gain calibration impedance load, a fine gain calibration impedance load, or a phase calibration impedance load.

6. The medical device of any of clauses 1-5, wherein the instrument head further includes a buffer circuit that couples an output of the one or more electrode pairs to the impedance bridge.

7. The medical device of any of clauses 1-6, wherein an output of the buffer circuit and an input of the impedance bridge are coupled by an analog-to-digital converter that converts the output of the buffer circuit to a digital output.

8. The medical device of any of clauses 1-7, further comprising a current generator that causes the one or more wire pairs to conduct current between the instrument head and the impedance bridge at one or more frequencies.

9. The medical device of any of clauses 1-8, further comprising a processor that measures at least one of a calibration impedance measurement associated with a current flowing between the impedance bridge and the calibration impedance at one or more frequencies or an impedance measurement associated with a current flowing between the impedance bridge and the one or more electrode pairs at one or more frequencies.

10. The medical device of any of clauses 1-9, further comprising a processor that determines at least one of a compensated impedance measurement based on one or more calibration impedance measurements and one or more impedance measurements or a property of a portion of tissue contacting the one or more electrode pairs.

11. In some embodiments, a method for determining a property of tissue comprises recording, at one or more frequencies, one or more calibration impedance measurements associated with a calibration impedance that is included in an instrument head of a medical device, recording, at one or more frequencies, one or more impedance measurements associated with one or more electrode pairs that are included in the instrument head, determining one or more compensated impedance measurements based on the one or more calibration impedance measurements and the one or more impedance measurements, and determining the property of the tissue based on the one or more compensated impedance measurements.

12. The method of clause 11, wherein recording the one or more calibration impedance measurements includes at least one of a phase offset based on a calibration impedance measurement of a calibration impedance load, a coarse gain based on a calibration impedance measurement of a coarse gain calibration impedance load, a fine gain based on a calibration impedance measurement of a fine gain calibration impedance load, or a phase based on a calibration impedance measurement of a phase calibration impedance load.

13. The method of any of clauses 11-12, wherein recording the one or more calibration impedance measurements includes one or both of, recording one or more of the one or more calibration impedance measurements during a factory calibration process, or recording one or more of the one or more calibration impedance measurements during a surgical calibration process.

14. The method of any of clauses 11-13, wherein recording the one or more calibration impedance measurements comprises measuring the one or more calibration impedance measurements of the calibration impedance at each frequency included in a first set of frequencies, and recording the one or more impedance measurements comprises measuring the one or more impedance measurements associated with the one or more electrode pairs at each frequency included in a second set of frequencies, wherein the second set of frequencies is different than the first set of frequencies.

15. The method of any of clauses 11-14, wherein recording the one or more impedance measurements comprises recording a first impedance measurement based on a first current associated with a first electrode pair and a first wire pair, and recording a second impedance measurement based on a second current associated with a second electrode pair and a second wire pair.

16. The method of any of clauses 11-15, wherein determining the one or more compensated impedance measurements includes one or both of, subtracting the one or more calibration impedance measurements from the one or more impedance measurements, or dividing the one or more impedance measurements by the one or more calibration impedance measurements.

17. The method of any of clauses 11-16, wherein determining the property of the tissue comprises determining a Cole relaxation frequency of the tissue based on the one or more compensated impedance measurements.

18. The method of any of clauses 11-17, wherein the Cole relaxation frequency corresponds to a frequency associated with a greatest compensated impedance measurement included in the one or more compensated impedance measurements.

19. The method of any of clauses 11-18, wherein determining the property of the tissue further comprises determining a tissue type of the tissue based on the Cole relaxation frequency of the tissue.

20. The method of any of clauses 11-19, wherein determining the property of the tissue comprises determining an aggressiveness of a tumor tissue based on the Cole relaxation frequency.

21. The method of any of clauses 11-20, wherein determining the property of the tissue comprises determining a tumor tissue type of the tissue based on a Cole relaxation frequency of the tissue being above a threshold frequency, and determining a non-tumor tissue type of the tissue based on the Cole relaxation frequency of the tissue being below the threshold frequency.

22. The method of any of clauses 11-21, further compris-
   ing presenting the property of the tissue of a medical
   device using at least one of a visual output or an audio
   output.
23. The method of any of clauses 11-22, further comprising controlling a tool of the instrument head based on
   the property of the tissue, the tool comprising at least
   one of a therapeutic drug delivery tool, an energy
   delivery tool, or a tissue sample extraction tool.
   Any and all combinations of any of the claim elements
recited in any of the claims and/or any elements described in
this application, in any fashion, fall within the contemplated
scope of the present invention and protection.
   The descriptions of the various embodiments have been
presented for purposes of illustration, but are not intended to
be exhaustive or limited to the embodiments disclosed.
Many modifications and variations will be apparent to those
of ordinary skill in the art without departing from the scope
and spirit of the described embodiments.
   Aspects of the present embodiments may be embodied as
a system, method or computer program product. Accord-
ingly, aspects of the present disclosure may take the form of
an entirely hardware embodiment, an entirely software
embodiment (including firmware, resident software, micro-
code, etc.) or an embodiment combining software and
hardware aspects that may all generally be referred to herein
as a "module," a "system," or a "computer." In addition, any
hardware and/or software technique, process, function, com-
ponent, engine, module, or system described in the present
disclosure may be implemented as a circuit or set of circuits.
Furthermore, aspects of the present disclosure may take the
form of a computer program product embodied in one or
more computer readable medium(s) having computer read-
able program code embodied thereon.
   Any combination of one or more computer readable
medium(s) may be utilized. The computer readable medium
may be a computer readable signal medium or a computer
readable storage medium. A computer readable storage
medium may be, for example, but not limited to, an elec-
tronic, magnetic, optical, electromagnetic, infrared, or semiconductor system, apparatus, or device, or any suitable
combination of the foregoing. More specific examples (a
non-exhaustive list) of the computer readable storage
medium would include the following: an electrical connec-
tion having one or more wires, a portable computer diskette,
a hard disk, a random access memory (RAM), a read-only
memory (ROM), an erasable programmable read-only
memory (EPROM or Flash memory), an optical fiber, a
portable compact disc read-only memory (CD-ROM), an
optical storage device, a magnetic storage device, or any
suitable combination of the foregoing. In the context of this
document, a computer readable storage medium may be any
tangible medium that can contain, or store a program for use
by or in connection with an instruction execution system,
apparatus, or device.
Aspects of the present disclosure are described above with
reference to flowchart illustrations and/or block diagrams of
methods, apparatus (systems) and computer program prod-
ucts according to embodiments of the disclosure. It will be
understood that each block of the flowchart illustrations
and/or block diagrams, and combinations of blocks in the
flowchart illustrations and/or block diagrams, can be imple-
mented by computer program instructions. These computer
program instructions may be provided to a processor of a
general purpose computer, special purpose computer, or
other programmable data processing apparatus to produce a
machine. The instructions, when executed via the processor of the computer or other programmable data processing
apparatus, enable the implementation of the functions/acts
specified in the flowchart and/or block diagram block or
blocks. Such processors may be, without limitation, general
purpose processors, special-purpose processors, application-
specific processors, or field-programmable gate arrays.
   The flowchart and block diagrams in the figures illustrate
the architecture, functionality, and operation of possible
implementations of systems, methods and computer pro-
gram products according to various embodiments of the
present disclosure. In this regard, each block in the flowchart
or block diagrams may represent a module, segment, or
portion of code, which comprises one or more executable
instructions for implementing the specified logical function
(s). It should also be noted that, in some alternative imple-
mentations, the functions noted in the block may occur out
of the order noted in the figures. For example, two blocks
shown in succession may, in fact, be executed substantially
concurrently, or the blocks may sometimes be executed in
the reverse order, depending upon the functionality
involved. It will also be noted that each block of the block
diagrams and/or flowchart illustration, and combinations of
blocks in the block diagrams and/or flowchart illustration,
can be implemented by special purpose hardware-based
systems that perform the specified functions or acts, or
combinations of special purpose hardware and computer
instructions.
   While the preceding is directed to embodiments of the
present disclosure, other and further embodiments of the
disclosure may be devised without departing from the basic
scope thereof, and the scope thereof is determined by the
claims that follow.

What is claimed is:
1. A method for determining a property of tissue, the
method comprising:
   recording, at one or more frequencies across an imped-
      ance bridge, one or more calibration impedance mea-
      surements that indicate an impedance of a first circuit
      that includes at least the impedance bridge, a calibra-
      tion impedance load that is included in an instrument
      head of a medical device, and a first wire pair that
      passes within a catheter of the medical device and that
      is electrically coupled to the calibration impedance
      load;
   recording, at one or more frequencies across the imped-
      ance bridge, one or more impedance measurements that
      indicate an impedance of a second circuit that includes
      at least the impedance bridge, one or more electrode
      pairs that are included in the instrument head, and a
      second wire pair that passes within the catheter and that
      is electrically coupled to the one or more electrode
      pairs;
   determining one or more compensated impedance mea-
      surements based on the one or more calibration imped-
      ance measurements and the one or more impedance
      measurements; and
   performing at least one action based on the one or more
      compensated impedance measurements.
2. Method of claim 1, wherein the calibration impedance
load includes one or more additional impedance loads, and
recording the one or more calibration impedance measure-
ments includes at least one of:
   a phase offset based on a calibration impedance measure-
      ment of a phase offset calibration impedance load
      included in the one or more additional impedance
      loads, a coarse gain based on a calibration impedance measurement of a coarse gain calibration impedance load included in the one or more additional impedance loads, a fine gain based on a calibration impedance measurement of a fine gain calibration impedance load included in the one or more additional impedance loads, or a phase based on a calibration impedance measurement of a phase calibration impedance load included in the one or more additional impedance loads.

3. The method of claim 1, wherein recording the one or more calibration impedance measurements includes one or both of:

recording one or more of the one or more calibration impedance measurements during a factory calibration process, or recording one or more of the one or more calibration impedance measurements during a surgical calibration process, wherein the instrument head is contacting the tissue during the surgical calibration process.

4. The method of claim 1, wherein:

recording the one or more calibration impedance measurements comprises measuring the one or more calibration impedance measurements of the calibration impedance at each frequency included in a first set of frequencies, recording the one or more impedance measurements comprises measuring the one or more impedance measurements associated with the one or more electrode pairs at each frequency included in a second set of frequencies, and the second set of frequencies is different than the first set of frequencies.

5. The method of claim 1, wherein recording the one or more impedance measurements comprises:

recording a first impedance measurement based on a first current associated with a first electrode pair and the second wire pair, wherein the second wire pair is electrically coupled to the first electrode pair; and recording a second impedance measurement based on a second current associated with a second electrode pair and a third wire pair that that passes within the catheter and that is electrically coupled to the second electrode pair.

6. The method of claim 1, wherein determining the one or more compensated impedance measurements includes one or both of:

subtracting the one or more calibration impedance measurements from the one or more impedance measurements, or dividing the one or more impedance measurements by the one or more calibration impedance measurements.

7. The method of claim 1, wherein performing at least one action based on the one or more compensated impedance measurements comprises determining a Cole relaxation frequency of the tissue.

8. The method of claim 7, wherein the Cole relaxation frequency corresponds to a frequency associated with a greatest compensated impedance measurement included in the one or more compensated impedance measurements.

9. The method of claim 8, wherein performing at least one action based on the one or more compensated impedance measurements further comprises determining a tissue type of the tissue based on the Cole relaxation frequency of the tissue.

10. The method of claim 1, wherein performing at least one action based on the one or more compensated impedance measurements comprises:

determining a tumor tissue type of the tissue based on a Cole relaxation frequency of the tissue being above a threshold frequency; or determining a non-tumor tissue type of the tissue based on the Cole relaxation frequency of the tissue being below the threshold frequency.

11. The method of claim 1, further comprising presenting, by the medical device, an output based on the one or more compensated impedance measurements, wherein the output comprises at least one of a visual output or an audio output.

12. The method of claim 1, wherein:

performing at least one action based on the one or more compensated impedance measurements comprises controlling a tool of the instrument head based on the property of the tissue, and the tool comprises at least one of a therapeutic drug delivery tool, an energy delivery tool, or a tissue sample extraction tool.

13. The method of claim 1, wherein the first wire pair is a twisted wire pair, and wherein the second wire pair is a twisted wire pair.

* * * * *